US00PP20881P2

(12) United States Plant Patent
White et al.

(10) Patent No.: US PP20,881 P2
(45) Date of Patent: Mar. 23, 2010

(54) ***HELLEBORUS* PLANT NAMED 'BLT03'**
(50) Latin Name: ***Helleborus niger*×*Helleborus sternii***
Varietal Denomination: BLT03

(75) Inventors: Robin White, Alresford (GB); Sue White, Alresford (GB)

(73) Assignee: Amazing Breeders Company B.V., Aalsmeer (NL)

( * ) Notice: Subject to any disclaimer, the term of this patent is extended or adjusted under 35 U.S.C. 154(b) by 0 days.

(21) Appl. No.: 12/316,451

(22) Filed: Dec. 12, 2008

(51) Int. Cl.
*A01H 5/00* (2006.01)

(52) U.S. Cl. ..... Plt./439
(58) Field of Classification Search ..... Plt./439
See application file for complete search history.

*Primary Examiner*—Kent L Bell
(74) *Attorney, Agent, or Firm*—C. A. Whealy

(57) ABSTRACT

A new and distinct cultivar of *Helleborus* plant named 'BLT03', characterized by its upright and mounded plant habit; strong and vigorous growth habit; relatively narrow leaflets; early and freely flowering habit; single purple and light green-colored flowers; and good garden performance.

1 Drawing Sheet

Botanical designation: *Helleborus niger*×*Helleborus sternii*

Cultivar denomination: 'BLT03'

BACKGROUND OF THE INVENTION

The present invention relates to a new and distinct cultivar of *Helleborus* plant, botanically known as *Helleborus niger*× *Helleborus sternii*, and hereinafter referred to by the name 'BLT03'.

The new *Helleborus* is a product of a planned breeding program in Hampshire, United Kingdom. The objective of the breeding program was to create new frost-tolerant *Helleborus* cultivars with unique and attractive flower coloration.

The new *Helleborus* plant originated from a cross-pollination in Hampshire, United Kingdom in 2001, of proprietary selection of *Helleborus niger*, not patented, as the female, or seed, parent with a proprietary selection of *Helleborus sternii*, not patented, as the male, or pollen, parent. The new *Helleborus* plant was discovered and selected by the Inventor as a single flowering plant from within the progeny of the stated cross-pollination grown in a controlled environment in Hampshire, United Kingdom in 2003.

Asexual reproduction of the new *Helleborus* plant by tissue culture in a controlled environment in The Netherlands since 2003, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'BLT03'. These characteristics in combination distinguish 'BLT03' as a new and distinct cultivar of *Helleborus:*

1. Upright and mounded plant habit.
2. Strong and vigorous growth habit.
3. Relatively narrow leaflets.

4. Early and freely flowering habit.
5. Single purple and light green-colored flowers.
6. Good garden performance.

Plants of the new *Helleborus* can be compared to plants of the parent selections. Plants of the new *Helleborus* are more freely flowering than plants of the female parent selection. Plants of the new *Helleborus* have larger flowers than plants of the male parent selection.

Plants of the new *Helleborus* can be compared to plants of *Helleborus niger*×*Helleborus sternii* 'HGC Silvermoon', disclosed in U.S. Plant Pat. No. 15,639. Plants of the new *Helleborus* differ primarily from plants of 'HGC Silvermoon' in the following characteristics:

1. Plants of the new *Helleborus* are more freely flowering than plants of 'HGC Silvermoon'.
2. Plants of the new *Helleborus* flower for a longer period of time than plants of 'HGC Silvermoon'.
3. Plants of the new *Helleborus* and 'HGC Silvermoon' differ in flower color as plants of 'HGC Silvermoon' have white to light green-colored flowers.

BRIEF DESCRIPTION OF THE PHOTOGRAPH

The accompanying colored photograph illustrates the overall appearance of the new *Helleborus* plant, showing the colors as true as it is reasonably possible to obtain in colored reproductions of this type. Colors in the photograph may differ slightly from the color values cited in the detailed botanical description which accurately describe the colors of the new *Helleborus* plant. The photograph comprises a side perspective view of a typical flowering plant of 'BLT03' grown in a container.

DETAILED BOTANICAL DESCRIPTION

The aforementioned photograph and following observations, measurements and values describe plants grown in Aalsmeer, The Netherlands in containers during the winter in an outdoor nursery and under conditions which closely approximate commercial *Helleborus* production. During the production of the plants, day temperatures ranged from 8° C. to 14° C. and night temperatures ranged from −2° C. to 8° C. Plants had been growing for one year when the photograph and the description were taken. In the following description, color references are made to The Royal Horticultural Society Colour Chart, 1995 Edition, except where general terms of ordinary dictionary significance are used.

Botanical classification: *Helleborus niger*×*Helleborus sternii* 'BLT03'.

Parentage:

*Female, or seed, parent.*—Proprietary selection of *Helleborus niger*, not patented.

*Male, or pollen, parent.*—Proprietary selection of *Helleborus sternii,* not patented.

Propagation:

*Type.*—By tissue culture.

*Root description.*—Thick, fleshy; white in color.

*Rooting habit.*—Dense.

Plant description:

*Plant form and growth habit.*—Herbaceous perennial. Upright and mounded plant habit; strong and vigorous growth habit.

*Plant height.*—About 30 cm to 40 cm.

*Plant diameter* (*area of spread*).—About 30 cm.

Foliage description:

*Arrangement.*—Palmately compound with five leaflets per leaf.

*Leaf length.*—About 9 cm to 12.5 cm.

*Leaf width.*—About 3 cm to 4.5 cm.

*Leaflet shape.*—Lanceolate.

*Leaflet apex.*—Acute.

*Leaflet base.*—Attenuate.

*Leaflet margin.*—Serrate.

*Leaflet texture, upper and lower surfaces.*—Smooth, glabrous; leathery.

*Leaflet venation pattern.*—Pinnate; reticulate.

*Leaflet color.*—Developing leaves, upper surface: Close to 147A suffused with close to 187A. Developing leaves, lower surface: Close to 187A. Fully developed leaves, upper surface: Close to 139A; venation, close to 144B. Fully developed leaves, lower surface: Close to 194A; venation, close to 176B.

*Petiole.*—Length: About 20 cm to 25.5 cm. Diameter: About 5 mm. Texture, upper and lower surfaces: Smooth, glabrous. Color, upper and lower surfaces: Close to 194A flecked with close to 176B.

Flower description:

*Flower arrangement and shape.*—Single rotate flowers arranged on cymes; flowers face outwardly to nodding. Freely flowering habit, about 18 to 24 flowers and flower buds per inflorescence. Petals transformed into nectaries.

*Fragrance.*—None detected.

*Natural flowering season.*—Long flowering period; plants flower from January to May in The Netherlands.

*Flower longevity on the plant.*—About three months; flowers persistent.

*Flower buds.*—Length: About 2 cm. Diameter: About 1 cm. Shape: Ovoid. Color: Close to 181A.

*Inflorescence size.*—Length: About 30 cm to 40 cm. Diameter: About 20 cm.

*Flowers.*—Diameter: About 5 cm. Depth (height): About 3 cm.

*Sepals.*—Arrangement: Five in a single whorl. Length: About 2 cm. Width: About 1.5 cm. Shape: Obovate. Apex: Obtuse. Base: Obtuse. Margin: Slightly serrate. Texture, upper and lower surfaces: Smooth, glabrous. Color: When opening, upper and lower surfaces: Bi-colored, close to 186D and 193A to 157C. Fully opened, upper and lower surfaces: Bi-colored, close to 186D and 193A to 157C.

*Peduncles.*—Strength: Strong. Length: About 30 cm. Diameter: About 3 mm. Aspect: About 90° from vertical. Texture: Smooth, glabrous. Color: Close to 194A overlain with close to 176B.

*Reproductive organs.*—Stamens: Quantity per flower: About 40. Anther shape: Elliptical. Anther length: About 1 mm. Anther color: Close to 4A. Pollen amount: None observed. Pistils: Quantity per flower: About five. Pistil length: About 1 cm. Stigma shape: Club-shaped. Stigma color: Close to 145C. Style length: About 1 cm. Style color: Close to 145C. Ovary color: Close to 145B. Nectaries: Arrangement: About 12 to 14. Length: About 1 cm. Diameter: About 3 mm. Color, immature and mature: Close to 141C. Seeds/fruits: Seed and fruit development have not been observed.

Garden performance: Plants of the new *Helleborus* have been observed to have good garden performance and to tolerate rain, wind and temperatures from about −10° C. to about 25° C.

Pathogen/pest resistance: Plants of the new *Helleborus* have been observed to be relatively tolerant to Mildews. Plants of the new *Helleborus* have not been shown to be resistant to pests and other pathogens common to *Helleborus*.

It is claimed:

1. A new and distinct *Helleborus* plant named 'BLT03' as illustrated and described.

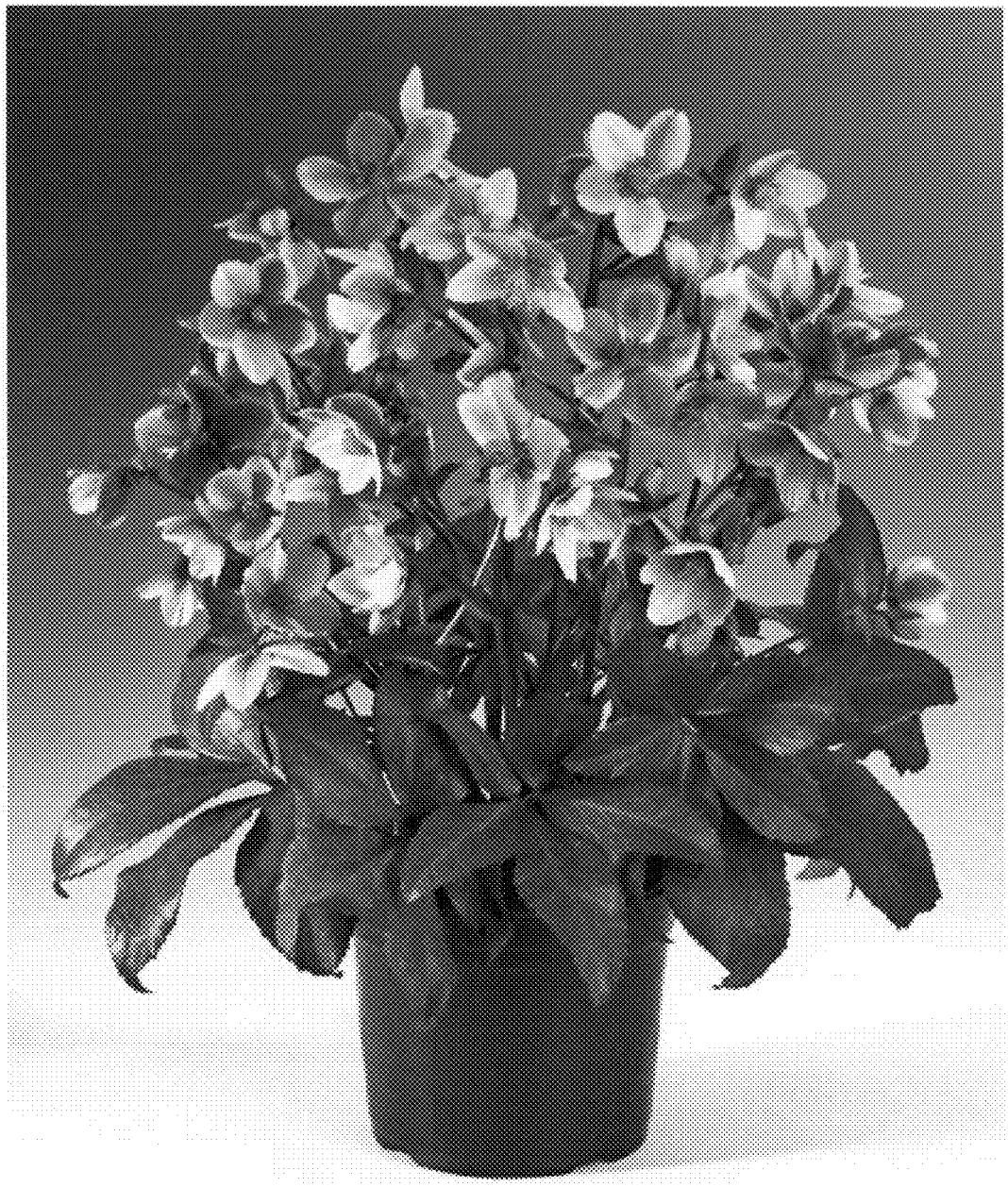

* * * * *